United States Patent
Sharma et al.

(10) Patent No.: US 11,957,692 B2
(45) Date of Patent: Apr. 16, 2024

(54) CLOMIPRAMINE FOR THE TREATMENT OF ALZHEIMER'S DISEASE

(71) Applicant: National Institute of Immunology, Delhi (IN)

(72) Inventors: Pushkar Sharma, Delhi (IN); Monika Chauhan, Delhi (IN)

(73) Assignee: National Institute of Immunology, New Delhi (IN)

( * ) Notice: Subject to any disclaimer, the term of this patent is extended or adjusted under 35 U.S.C. 154(b) by 0 days.

(21) Appl. No.: 17/751,613

(22) Filed: May 23, 2022

(65) Prior Publication Data

US 2023/0372356 A1 Nov. 23, 2023

(51) Int. Cl.
 *C07D 223/28* (2006.01)
 *A61K 31/55* (2006.01)
 *A61P 25/28* (2006.01)

(52) U.S. Cl.
 CPC .............. *A61K 31/55* (2013.01); *A61P 25/28* (2018.01)

(58) Field of Classification Search
 CPC ........ C07D 223/25; A61K 31/55; A61P 25/28
 See application file for complete search history.

(56) References Cited

FOREIGN PATENT DOCUMENTS

| CN | 111671721 A | 9/2020 |
|---|---|---|
| EP | 3090732 A1 | 9/2016 |
| JP | 211217190 A | 9/2012 |
| WO | 2004045718 A2 | 6/2004 |
| WO | 2005115471 A2 | 12/2005 |

OTHER PUBLICATIONS

Abdel-Salam et al., Study of the Effect of Antidepressant Drugs and Donepezil on Aluminum-Induced Memory Impairment and Biochemical Alterations in Rats, Comparative Clinical Path, vol. 24, No. 4, pp. 847-860 (Year: 2015).*

Mendez, Mario F. "The Relationship Between Anxiety and Alzheimer's Disease" Journal of Alzheimer's Disease Reports, 2021, 171-177.

Cedarbaum, Jesse M. et al., "Rationale for use of the Clinical Dementia Rating Sum of Boxes as a primary outcome measure for Alzheimer's disease clinical trials" Alzheimer's & Dimentia 9, 2013, S45-S55.

O'Bryant, Side E., et al., "Staging Dementia Using Clinical Demntia Rating Scale Sum of Boxes Scores: A Texas Alzheimer's Research Consortium Study", Arch Nerol. Aug. 2008; 65 (8) 1091-1095.

Chauhan, Monika, et al., "Aberrant activation of neuronal cell cycle caused by dysregulation of ubiquitin ligase Itch results in neurodegenration", Cell Death & Disease, 2020, 11:441.

Rossi, M., et al., "High throughput screening for inhibitors of the HECT ubiquitin E3 ligase ITCH identifies antidepressant drugs as regulators of autophagy", Cell Death and Disease, 2014, 5, e1203.

Yang Alvin, et al., "Differential effect of clomipramine on habituation and prepulse inhibition in dominant versus subordinate rats", European Neuropsychopharmacology, 2016, 26, 591-601.

Trappler, Brian "Treatment of Obsessive-Compulsive Disorder Using Clomipramine in a Very Old Patient", Annals of Pharmacotherapy, Jun. 1, 1999.

Cavaliere, Federica, et al., "The tricyclic antidepressant clomipramine inhibits neuronal atuophagic flux", "www.nature.com/scientficreports", published Mar. 19, 2019, Scientific Reports 2019, 9:4881.

Potjewyd, Frances M., et al., "Exploration of Aberrant E3 Ligases Implicated in Alzheimer's Disease and Development of Chemical Tools to Modulate Their Function", Frontiers in Cellular Neuroscience Nov. 18, 2021, vol. 15, Article 768655.

"Metals, aluminum, and dementia" Alzheimer's Society, https://www.alzheimers.org.uk/about-dementia/risk-factors-and-prevention/metals-and-dementia, accessed Nov. 3, 2023.

Drummond, et al. "Alzheimer's disease: experimental models and reality" Acta Neuropathol, Dec. 26, 2016, DOI 10.1007/s00401-016-1662-x.

Games, et al. "Alzheimer-type neuropathology in transgenic mice overexpressing V717F B-amylold precursor protein" Letters to Nature, vol. 373, Feb. 9, 1995, p. 523-527.

Yokoyama, et al. "Mouse Models of Alzheimer's Disease" Frontiers in Molecular Neuroscience, Jun. 21, 2022, vol. 15, Article 912995, doi: 10.3389/fnmol.2022.912995.

* cited by examiner

*Primary Examiner* — Brenda L Coleman

(74) *Attorney, Agent, or Firm* — Conley Rose, P.C.

(57) ABSTRACT

The present disclosure provides methods for treating Alzheimer's disease (AD) comprising administering clomipramine or a pharmaceutically acceptable salt thereof. The administration of clomipramine increases the levels of TAp73 and decreases the levels of proliferating cell nuclear antigen (PCNA) and cleaved caspase-3 in the AD patients. The methods of the present disclosure reduce the neurodegeneration and improve the cognitive and functional decline in AD patients.

17 Claims, 12 Drawing Sheets

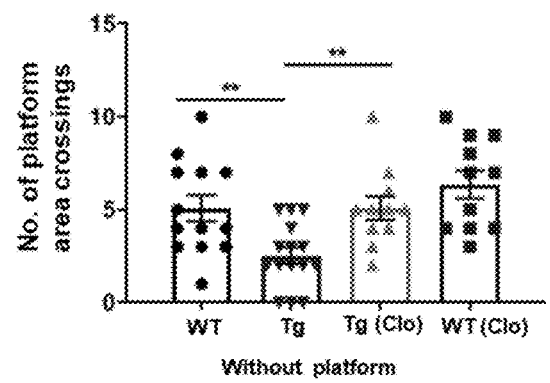
FIG. 5B
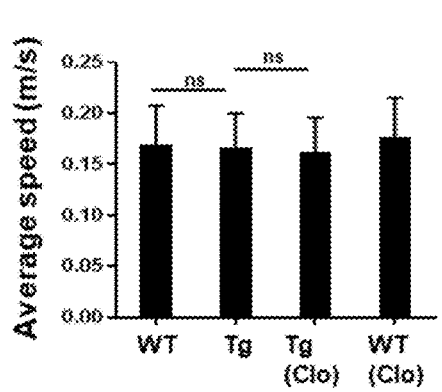
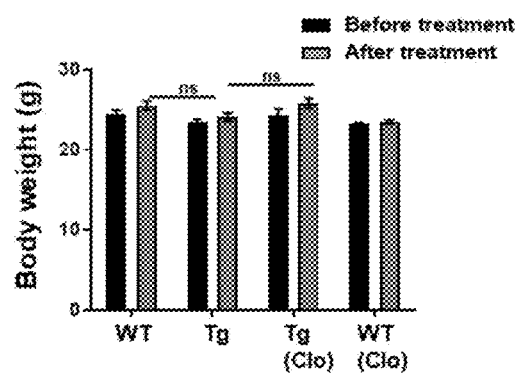
FIG. 6A
FIG. 6B

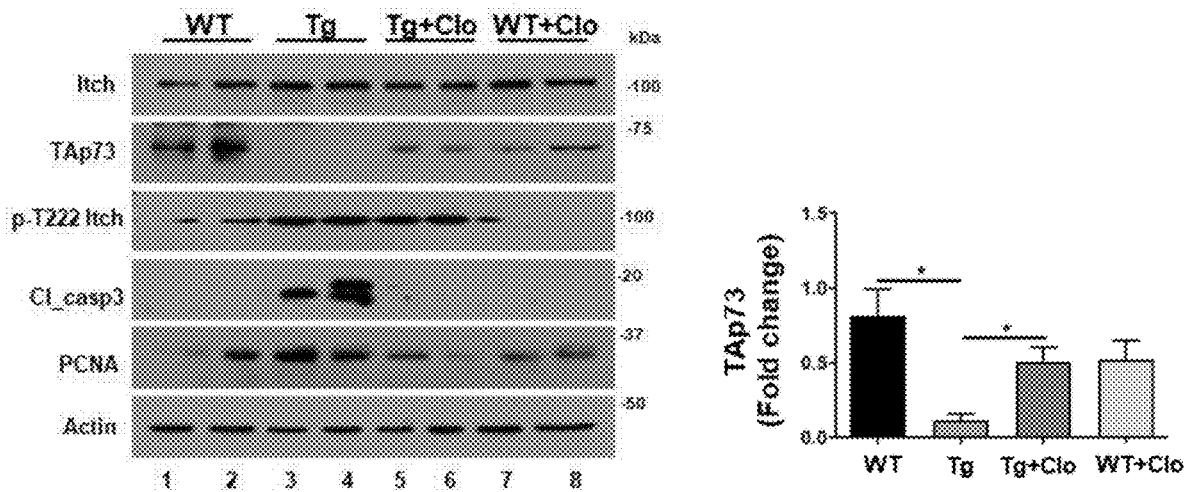
FIG. 9A
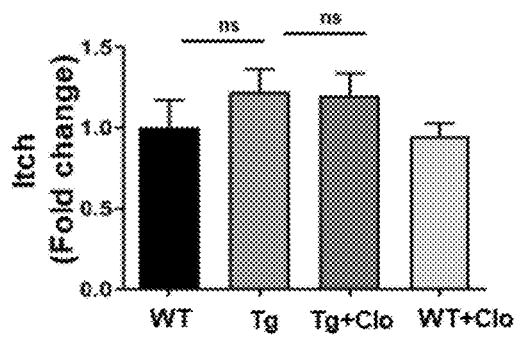
FIG. 9B
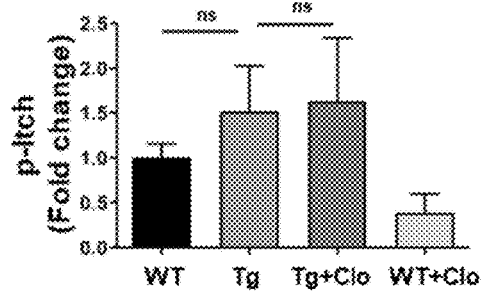
FIG. 9C
FIG. 9D
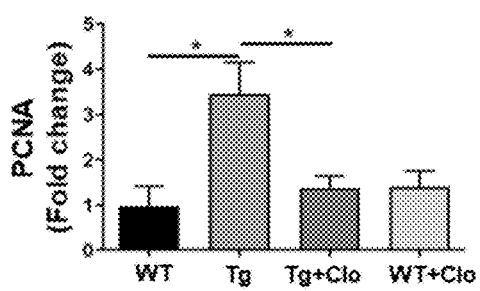
FIG. 9E
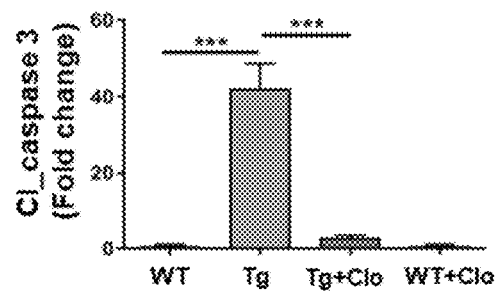
FIG. 9F

CLOMIPRAMINE FOR THE TREATMENT OF ALZHEIMER'S DISEASE

FIELD OF THE DISCLOSURE

The present invention relates to methods for treating Alzheimer's Disease. In particular, the present invention relates to use of clomipramine or a pharmaceutically acceptable salt thereof for treating cognitive and/or functional impairment in patients with Alzheimer's Disease.

BACKGROUND OF THE DISCLOSURE

Alzheimer's Disease (AD) is a neurodegenerative disease characterized by a progressive decline in cognitive function and in an ability to perform daily living activities (functional decline). AD is a heterogenous disease, i.e., clinical and biological changes exhibited by individual patients vary from a patient to patient. However, the loss of neurons or neurodegeneration is the major and the common cause of disease pathogenesis, which needs to be addressed to develop a cure for this disease. A number of therapeutic interventions are being explored as a treatment for AD; however, till date there has been no effective treatment that can inhibit or reduce the neurodegeneration and reverse the decline in the cognitive function. The present disclosure provides methods for treating AD patients that reduce the neurodegeneration and provide a substantial improvement in cognitive, learning, memory and/or functional abilities of the AD patients.

SUMMARY OF THE DISCLOSURE

The present disclosure provides a method for treating AD in a patient in need thereof, comprising administering to the patient clomipramine or a pharmaceutically acceptable salt thereof.

The present disclosure provides a method for reducing neurodegeneration in a patient suffering from AD or at a risk of developing AD, comprising administering to the patient clomipramine or a pharmaceutically acceptable salt thereof.

The present disclosure provides a method for treating an AD patient having a cognitive impairment but minimal or no anxiety, comprising administering to the patient clomipramine or a pharmaceutically acceptable salt thereof.

The present disclosure provides a method for treating a mild cognitive impairment (MCI) in a patient, comprising administering to the patient clomipramine or a pharmaceutically acceptable salt thereof.

The present disclosure also provides a method of treating an AD patient having (i) a Clinical Dementia Rating Scale Sum of Boxes (CDR-SOB) score from 4.5 to 9.0, or (ii) CDR-SOB score from 9.5 to 15.5, or (iii) CDR-SOB score from 16-18, comprising administering to the patient clomipramine or a pharmaceutically acceptable salt thereof.

The present disclosure also provides a method for treating a pre-clinical stage AD in a patient, comprising administering to the patient clomipramine or a pharmaceutically acceptable salt thereof.

The present disclosure provides use of clomipramine or a pharmaceutically acceptable salt thereof for treating various clinical stages of AD as described herein.

The present disclosure provides clomipramine or a pharmaceutically acceptable salt thereof or use as a medicament for treatment of various clinical stages of AD as described herein.

BRIEF DESCRIPTION OF THE DRAWINGS

FIG. 5B shows the results of the Morris water maze test without platform of WT and TgAD mice treated with clomipramine.

FIG. 6A shows an average swimming speed of WT and TgAD mice treated with clomipramine.

FIG. 6B shows body weights of WT and TgAD mice treated with clomipramine.

FIG. 9A shows a Western blot of lysates obtained from the cortex region of the brain of WT and TgAD mice treated with clomipramine.

FIG. 9B shows the quantification of the levels of TAp73 from the Western blot of FIG. 9A.

FIG. 9C shows the quantification of the levels of Itch from the Western blot of FIG. 9A.

FIG. 9D shows the quantification of the levels of phosphorylated Itch from the Western blot of FIG. 9A.

FIG. 9E shows the quantification of the levels of PCNA from the Western blot of FIG. 9A.

FIG. 9F shows the quantification of the levels of cleaved Caspase-3 from the Western blot of FIG. 9A.

DETAILED DESCRIPTION OF THE DISCLOSURE

Figure 1A:
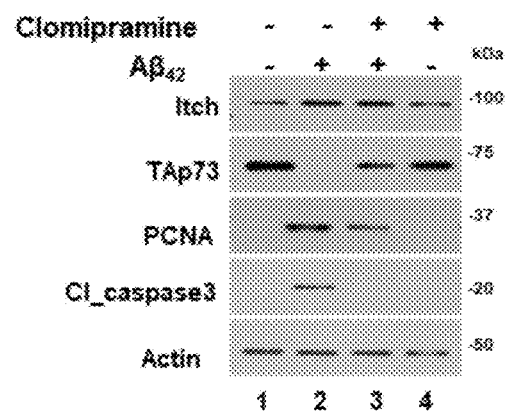
FIG. 1A shows a Western blot of lysates obtained from rat cortical neurons treated with Aβ-42 peptide followed by clomipramine.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The use of the expression "at least" or "at least one" suggests the use of one or more elements or ingredients or quantities, as the use may be in the embodiment of the disclosure to achieve one or more of the desired objects or results. Throughout this specification, the word "comprise", or variations such as "comprises" or "comprising" or "containing" or "has" or "having", or "including but not limited to" wherever used, will be understood to imply the inclusion of a stated element, integer or step, or group of elements, integers or steps, but not the exclusion of any other element, integer or step, or group of elements, integers or steps.

Reference throughout this specification to "one embodiment", "an embodiment", or "some embodiments" means that a particular feature, structure or characteristic described in connection with the embodiment may be included in at least one embodiment of the present disclosure. Thus, the appearances of the phrases "in one embodiment", "in an embodiment", or "in some embodiments" in various places throughout this specification may not necessarily all refer to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

The term "subject" or "patient" as used herein refers to any mammal including, without limitation, humans and other primates (e.g., chimpanzees and other apes and monkey species), farm animals (e.g., cattle, sheep, pigs, goats and horses), domestic mammals (e.g., dogs and cats), and laboratory animals (e.g., rodents such as mice, rats, and guinea pigs). In some embodiments, the patient is a mammal. In some embodiments, the patient is a human.

Terminally differentiated neurons exit the cell cycle and remain in this quiescent state for lifetime. During neurodegeneration manifested in AD, a significant number of these neurons, upon encountering neurotoxicity try to re-enter the cell cycle but instead undergo apoptosis (Park, Obeidat et al. 2000, Modi, Komaravelli et al. 2012). In AD, th eaccumulation of Aβ42 neurotoxic peptide triggers the activation of various signaling cascades detrimental to the survival of neurons (Zhu, Castellani et al. 2001, Modi, Komaravelli et al. 2012). The present inventors found that A4β2 induced JNK pathway activation in AD results in an aberrant activation of a HECT family E3 ubiquitin ligase, Itch, leading to the proteasomal degradation of a transcription factor, TAp73, and induction of a cell cycle related neuronal apoptosis (CRNA). The inventors found that clomipramine can restore the levels of TAp73 and reduce CRNA thereby inhibiting or reducing neurodegeneration observed in AD. Further, the inventors observed that an administration of clomipramine improves memory and cognitive function in a mouse model of AD.

The present disclosure provides a method for treating AD in a patient, comprising administering to the patient clomipramine or a pharmaceutically acceptable salt thereof. In some embodiments, the pharmaceutically acceptable salt of clomipramine is clomipramine hydrochloride.

In some embodiments, the administration of clomipramine to the patient inhibits degradation of TAp73 in neuronal cells of the patient. Accordingly, in some embodiments, provided herein is a method of inhibiting degradation of TAp73 in neuronal cells of a subject comprising administering to the patient clomipramine or a pharmaceutically acceptable salt thereof. In some embodiments, clomipramine inhibits degradation of TAp73by about 0.5 to about 4-fold, including values and ranges thereof, compared to levels of TAp73 prior to administration of clomipramine. In some embodiments, the administration of clomipramine inhibits degradation of TAp73 in neuronal cells by about 0.5 to about 3.5-fold, about 0.5 to about 3-fold, about 0.5 to 2.5-fold, about 0.5 to about 2-fold, about 0.5 to about 1.5-fold, about 0.5 to about 1-fold, about 1 to about 4-fold, about 1 to about 3.5-fold, about 1 to about 3-fold, about 1 to about 2.5-fold, about 1 to about 2-fold, about 1 to about 1.5-fold, about 1.5 to about 4-fold, about 1.5 to about 3.5-fold, about 1.5 to about 3-fold, about 1.5 to about 2.5-fold, about 1.5 to about 2-fold, about 2 to about 4-fold, about 2 to about 3.5-fold, about 2 to about 3-fold, about 2 to about 2.5-fold, about 2.5 to about 4-fold, about 2.5 to about 3.5-fold, about 2.5 to about 3-fold, about 3 to about 4-fold, about 3 to about 3.5-fold, or about 3.5 to about 4-fold, including values and ranges thereof, compared to levels of TAp73 prior to administration of clomipramine. In some embodiments, the administration of clomipramine inhibits degradation of TAp73 in neuronal cells by about 0.5-fold, 1-fold, 1.3-fold, 1.4-fold, 1.5-fold, 1.7-fold, 1.8-fold, 2-fold, 2.3-fold, 2.4-fold, 2.5-fold, 2.8-fold, 3-fold, 3.2-fold, 3.4-fold, 3.5-fold, 3.7-fold, or by about 4-fold, compared to levels of TAp73 prior to administration of clomipramine.

In some embodiments, the administration of clomipramine inhibits degradation of TAp73 in neuronal cells by about 20-80%, including values and ranges thereof, compared to levels of TAp73 prior to administration of clomipramine. In some embodiments, the administration of clomipramine inhibits degradation of TAp73 in neuronal cells by about 20-75%, 20-70%, 20-65%, 20-60%, 20-55%, 20-50%, 20-45%, 20-40%, 20-30%, 25-80%, 25-75%, 25-70%, 25-65%, 25-60%, 25-55%, 25-50%, 25-45%, 25-40%, 25-35%, 30-80%, 30-75%, 30-70%, 30-65%, 30-60%, 30-55%, 30-50%, 30-45%, 35-80%, 35-75%, 35-70%, 35-65%, 35-60%, 35-55%, 35-50%, 40-80%, 40-75%, 40-70%, 40-65%, 40-60%, 40-50%, 50-80%, 50-75%, 50-70%, 50-65%, 50-60%, 60-80%, 60-75%, 60-70%, 65-80%, or 70-80%, including values and ranges thereof, compared to levels of TAp73 prior to administration of clomipramine. In some embodiments, the administration of clomipramine inhibits degradation of TAp73 in neuronal cells by about 20%, 25%, 30%, 35%, 40%, 45%, 50%, 55%, 60%, 65%, 70%, 75%, or about 80%, including values and ranges thereof, compared to levels of TAp73 prior to administration of clomipramine.

In some embodiments, the administration of clomipramine to the patient increases levels of TAp73 in neuronal cells of the patient, compared to levels of TAp73 prior to administration of clomipramine. Accordingly, in some embodiments, provided herein is a method of increasing levels of TAp73 in neuronal cells of a subject comprising administering to the patient clomipramine or a pharmaceutically acceptable salt thereof. In some embodiments, the administration of clomipramine to the patient increases levels of TAp73 by about 0.5 to about 4-fold, including values and ranges thereof, compared to levels of TAp73 prior to administration of clomipramine. In some embodiments, the administration of clomipramine increases levels of TAp73 in neuronal cells by about 0.5 to about 3.5-fold, about 0.5 to about 3-fold, about 0.5 to 2.5-fold, about 0.5 to about 2-fold, about 0.5 to about 1.5-fold, about 0.5 to about 1-fold, including values and ranges thereof, compared to levels of TAp73 prior to administration of clomipramine. In some embodiments, the administration of clomipramine increases levels of TAp73 in neuronal cells by about 0.5-fold, 1-fold, 1.3-fold, 1.4-fold, 1.5-fold, 1.7-fold, 1.8-fold, 2-fold, 2.3-fold, 2.4-fold, 2.5-fold, 2.8-fold, 3-fold, 3.2-fold, 3.4-fold, 3.5-fold, 3.7-fold, or by about 4-fold, compared to levels of TAp73 prior to administration of clomipramine.

In some embodiments, the administration of clomipramine to the patient increases levels of TAp73 in neuronal cells of the patient by about 20-80%, including values and ranges thereof, compared to levels of TAp73 prior to administration of clomipramine. In some embodiments, the administration of clomipramine increases levels of TAp73 in neuronal cells by about 20-75%, 20-70%, 20-65%, 20-60%, 20-55%, 20-50%, 20-45%, 20-40%, 20-30%, 25-80%, 25-75%, 25-70%, 25-65%, 25-60%, 25-55%, 25-50%, 25-45%, 25-40%, 25-35%, 30-80%, 30-75%, 30-70%, 30-65%, 30-60%, 30-55%, 30-50%, 30-45%, 35-80%, 35-75%, 35-70%, 35-65%, 35-60%, 35-55%, 35-50%, 40-80%, 40-75%, 40-70%, 40-65%, 40-60%, 40-50%, 50-80%, 50-75%, 50-70%, 50-65%, 50-60%, 60-80%, 60-75%, 60-70%, 65-80%, or 70-80%, including values and ranges thereof, compared to levels of TAp73 prior to administration of clomipramine. In some embodiments, the administration of clomipramine increases levels of TAp73 in neuronal cells by about 20%, 25%, 30%, 35%, 40%, 45%, 50%, 55%, 60%, 65%, 70%, 75%, or about 80%, including values and ranges thereof, compared to levels of TAp73 prior to administration of clomipramine.

In some embodiments, the administration of clomipramine to the patient inhibits cell cycle related neuronal apoptosis (CRNA) in the patient. Accordingly, in some embodiments, the present disclosure provides a method for inhibiting CRNA in a subject comprising administering to the subject clomipramine or a pharmaceutically acceptable salt thereof. In some embodiments, the levels of proliferating cell nuclear antigen (PCNA) or the levels of cleaved caspase 3 in neuronal cells of the patient are employed to measure the extent of CRNA.

In some embodiments, the administration of clomipramine inhibits CRNA in the neuronal cells of the patient by about 0.5 to about 5-fold, including values and ranges thereof, as measured by a decrease in levels of PCNA when compared to levels of PCNA prior to administration of clomipramine. That is, in this embodiment, the administration of clomipramine to a patient decreases levels of PCNA by about 0.5 to about 5-fold, including values and ranges thereof, in the neuronal cells of the patient, compared to levels of PCNA prior to administration of clomipramine. In some embodiments, the administration of clomipramine to a patient decreases levels of PCNA by about 0.5 to about 4.5-fold, about 0.5 to about 4-fold, about 0.5 to about 3.5-fold, about 0.5 to about 3-fold, about 0.5 to 2.5-fold, about 0.5 to about 2-fold, about 0.5 to about 1.5-fold, about 0.5 to about 1-fold, about 1 to about 5-fold, about 1 to about 4.5-fold, about 1 to about 4-fold, about 1 to about 3.5-fold, about 1 to about 3-fold, about 1 to about 2.5-fold, about 1 to about 2-fold, about 1 to about 1.5-fold, about 1.5 to about 5-fold, about 1.5 to about 4.5-fold, about 1.5 to about 4-fold, about 1.5 to about 3.5-fold, about 1.5 to about 3-fold, about 1.5 to about 2.5-fold, about 1.5 to about 2-fold, about 2 to about 5-fold, about 2 to about 4.5-fold, about 2 to about 4-fold, about 2 to about 3.5-fold, about 2 to about 3-fold, about 2 to about 2.5-fold, about 2.5 to about 5-fold, about 2.5 to about 4.5-fold, about 2.5 to about 4-fold, about 2.5 to about 3.5-fold, about 2.5 to about 3-fold, about 3 to about 5-fold, about 3 to about 4.5-fold, about 3 to about 4-fold, about 3 to about 3.5-fold, about 3.5 to about 5-fold, about 3.5 to about 4.5-fold, about 3.5 to about 4-fold, or by about 4 to about 5-fold, including values and ranges thereof, compared to levels of PCNA prior to administration of clomipramine. In some embodiments, the administration of clomipramine to a patient decreases levels of PCNA by about 0.5-fold, 1-fold, 1.3-fold, 1.5-fold, 1.8-fold, 2-fold, 2.3-fold, 2.5-fold, 2.8-fold, 3-fold, 3.3-fold, 3.5-fold, 4-fold, 4.3-fold, 4.5-fold, 4.8-fold, or by about 5-fold, compared to levels of PCNA prior to administration of clomipramine.

In some embodiments, the administration of clomipramine to the patient inhibits CRNA in the patient by about 20-90%, including values and ranges thereof, as measured by a decrease in levels of PCNA when compared to levels of PCNA prior to administration of clomipramine. That is, in this embodiment, the administration of clomipramine to a patient decreases levels of PCNA by about 20-90%, including values and ranges thereof, in neuronal cells of the patient, compared to levels of PCNA prior to administration of clomipramine. In some embodiments, the administration of clomipramine to a patient decreases levels of PCNA by about 20-90%, about 20-80%, 20-75%, 20-70%, 20-65%, 20-60%, 20-55%, 20-50%, 20-45%, 20-40%, 20-30%, 25-90%, 25-85%, 25-80%, 25-75%, 25-70%, 25-65%, 25-60%, 25-55%, 25-50%, 25-45%, 25-40%, 25-35%, 30-90%, 30-85%, 30-80%, 30-75%, 30-70%, 30-65%, 30-60%, 30-55%, 30-50%, 30-45%, 35-90%, 35-85%, 35-80%, 35-75%, 35-70%, 35-65%, 35-60%, 35-55%, 35-50%, 40-90%, 40-85%, 40-80%, 40-75%, 40-70%, 40-65%, 40-60%, 40-50%, 50-90%, 50-85%, 50-80%, 50-75%, 50-70%, 50-65%, 50-60%, 60-90%, 60-85%, 60-80%, 60-75%, 60-70%, 65-90%, 65-85%, 65-80%, 70-90%, or 70-80%, including values and ranges thereof, compared to levels of PCNA prior to administration of clomipramine. In some embodiments, the administration of clomipramine to a patient decreases levels of PCNA by about 20%, 25%, 30%, 35%, 40%, 45%, 50%, 55%, 60%, 65%, 70%, 75%, 80%, 85%, or by about 90%, including values and ranges thereof, compared to levels of PCNA prior to administration of clomipramine.

In some embodiments, the administration of clomipramine inhibits CRNA in the neuronal cells of the patient by about 0.5 to about 5-fold, including values and ranges thereof, as measured by a decrease in levels of cleaved caspase-3 when compared to levels of cleaved caspase-3 prior to administration of clomipramine. That is, in this embodiment, the administration of clomipramine to a patient decreases levels of cleaved caspase-3 by about 0.5 to about 5-fold, including values and ranges thereof, in the neuronal cells of the patient, compared to levels of cleaved caspase-3 prior to administration of clomipramine. In some embodiments, the administration of clomipramine to a patient decreases levels of cleaved caspase-3 by about 0.5 to about 4.5-fold, about 0.5 to about 4-fold, about 0.5 to about 3.5-fold, about 0.5 to about 3-fold, about 0.5 to 2.5-fold, about 0.5 to about 2-fold, about 0.5 to about 1.5-fold, about 0.5 to about 1-fold, about 1 to about 5-fold, about 1 to about 4.5-fold, about 1 to about 4-fold, about 1 to about 3.5-fold, about 1 to about 3-fold, about 1 to about 2.5-fold, about 1 to about 2-fold, about 1 to about 1.5-fold, about 1.5 to about 5-fold, about 1.5 to about 4.5-fold, about 1.5 to about 4-fold, about 1.5 to about 3.5-fold, about 1.5 to about 3-fold, about 1.5 to about 2.5-fold, about 1.5 to about 2-fold, about 2 to about 5-fold, about 2 to about 4.5-fold, about 2 to about 4-fold, about 2 to about 3.5-fold, about 2 to about 3-fold, about 2 to about 2.5-fold, about 2.5 to about 5-fold, about 2.5 to about 4.5-fold, about 2.5 to about 4-fold, about 2.5 to about 3.5-fold, about 2.5 to about 3-fold, about 3 to about 5-fold, about 3 to about 4.5-fold, about 3 to about 4-fold, about 3 to about 3.5-fold, about 3.5 to about 5-fold, about 3.5 to about 4.5-fold, about 3.5 to about 4-fold, or by about 4 to about 5-fold, including values and ranges thereof, compared to levels of cleaved caspase-3 prior to administration of clomipramine. In some embodiments, the administration of clomipramine to a patient decreases levels of cleaved caspase-3 by about 0.5-fold, 1-fold, 1.3-fold, 1.5-fold, 1.8-fold, 2-fold, 2.3-fold, 2.5-fold, 2.8-fold, 3-fold, 3.3-fold, 3.5-fold, 4-fold, 4.3-fold, 4.5-fold, 4.8-fold, or by about 5-fold, compared to levels of cleaved caspase-3 prior to administration of clomipramine.

In some embodiments, the administration of clomipramine to the patient inhibits CRNA in the patient by about 20-90%, including values and ranges thereof, as measured by a decrease in levels of cleaved caspase-3 when compared to levels of cleaved caspase-3 prior to administration of clomipramine. That is, in this embodiment, the administration of clomipramine to a patient decreases levels of cleaved caspase-3 by about 20-90%, including values and ranges thereof, in neuronal cells of the patient, compared to levels of cleaved caspase-3 prior to administration of clomipramine. In some embodiments, the administration of clomipramine to a patient decreases levels of cleaved caspase-3 by about 20-90%, about 20-80%, 20-75%, 20-70%, 20-65%, 20-60%, 20-55%, 20-50%, 20-45%, 20-40%, 20-30%, 25-90%, 25-85%, 25-80%, 25-75%, 25-70%, 25-65%, 25-60%, 25-55%, 25-50%, 25-45%, 25-40%, 25-35%, 30-90%, 30-85%, 30-80%, 30-75%, 30-70%, 30-65%, 30-60%, 30-55%, 30-50%, 30-45%, 35-90%, 35-85%, 35-80%, 35-75%, 35-70%, 35-65%, 35-60%, 35-55%, 35-50%, 40-90%, 40-85%, 40-80%, 40-75%, 40-70%, 40-65%, 40-60%, 40-50%, 50-90%, 50-85%, 50-80%, 50-75%, 50-70%, 50-65%, 50-60%, 60-90%, 60-85%, 60-80%, 60-75%, 60-70%, 65-90%, 65-85%, 65-80%, 70-90%, or 70-80%, including values and ranges thereof, compared to levels of cleaved caspase-3 prior to administration of clomipramine. In some embodiments, the administration of clomipramine to a patient decreases levels of cleaved caspase-3 by about 20%, 25%, 30%, 35%, 40%, 45%, 50%, 55%, 60%, 65%, 70%, 75%, 80%, 85%, or by about 90%, including values and ranges thereof, compared to levels of cleaved caspase-3 prior to administration of clomipramine.

The administration of clomipramine or a pharmaceutically acceptable salt thereof to a subject reduces the rate of neurodegeneration in the subject as measured by a decrease in the levels of PCNA or cleaved caspase-3 in the neuronal cells of the subject or by an increase in the levels of TAp73 in the neuronal cells of the subject. Accordingly, provided herein is a method of reducing neurodegeneration in a patient suffering from AD or at a risk of developing AD, comprising administering to the patient clomipramine or a pharmaceutically acceptable salt thereof. The rate or the extent of neurodegeneration can be measured by measuring the levels of TAp73, PCNA, cleaved caspase-3 in a sample obtained from the subject.

Alzheimer's disease has a spectrum of clinical stages depending on the severity of cognitive and/or functional impairment. Some of the clinical stages of AD include, but are not limited to, a pre-clinical stage, mild cognitive impairment (MCI), mild AD, moderate AD, and an advanced AD. In some embodiments, the present disclosure provides a method for treating a subject having a pre-clinical stage of AD, comprising administering to the subject clomipramine or a pharmaceutically acceptable salt thereof. In some embodiments, the present disclosure provides a method for treating a subject having a mild cognitive impairment (MCI), comprising administering to the subject clomipramine or a pharmaceutically acceptable salt thereof.

Various scoring systems have been developed to assess the extent of cognitive and functional impairment in AD patients. One of the scoring systems is CDR-SOB or CDR-SB. A Clinical Dementia Rating Sum of Boxes (CDRSOB or CDR-SB) is a composite score assessing both cognitive function and daily living activities. The score ranges from 0 to 18, and is calculated by summing over scores in six domains including memory, orientation, judgment/problem solving, community affairs, home and hobbies, and personal care, with higher scores indicative of more severe disease (Evans et al., "The importance of endpoint selection: How effective does a drug need to be for success in a clinical trial of a possible Alzheimer's disease treatment?", European Journal of Epidemiology (2018) 33:635-644). Patients having CDR-SOB scores from 4.5 to 9.0 are considered to have mild AD, patients having CDR-SOB scores from 9.5 to 15.5 are considered to have moderate AD, and patients having CDR-SOB scores from 16-18 are considered to have advanced AD (O'Bryant et al., "Staging Dementia Using Clinical Dementia Rating Scale Sum of Boxes Scores", Arch Neurol. 2008 August; 65(8): 1091-1095).

In some embodiments, the present disclosure provides a method for treating a subject having a CDR-SOB score from 4.5 to 9.0, comprising administering to the subject clomipramine or a pharmaceutically acceptable salt thereof. In some embodiments, the present disclosure provides a method for treating a subject having a CDR-SOB score from 9.5 to 15.5, comprising administering to the subject clomipramine or a pharmaceutically acceptable salt thereof. In some embodiments, the present disclosure provides a method for treating a subject having a CDR-SOB score from 16 to 18, comprising administering to the subject clomipramine or a pharmaceutically acceptable salt thereof.

While AD is a neurodegenerative disease, AD patients are likely to exhibit neuropsychiatric symptoms such as apathy, depression, and/or anxiety. However, all these symptoms may not be present in every AD patient. For example, some AD patients may exhibit apathy and/or depression, while some other patients may exhibit anxiety. It is estimated that anxiety is prevalent in about 40% of AD patients (Mendez et al., "The Relationship Between Anxiety and Alzheimer's Disease", Journal of Alzheimer's Disease Reports 5, 2021, 171-177). Anxiety is not known to be the cause of AD, which is mainly caused by neurodegeneration, it may be an outcome of AD like it is the case with several other diseases. In some embodiments, the present disclosure provides a method for treating an Alzheimer's disease patient having a cognitive impairment but minimal or no anxiety, comprising administering to the subject clomipramine or a pharmaceutically acceptable salt thereof. In some embodiments, the present disclosure provides a method for treating an Alzheimer's disease patient having a cognitive impairment but minimal or no depression, comprising administering to the subject clomipramine or a pharmaceutically acceptable salt thereof. In some embodiments, the present disclosure provides a method for treating an Alzheimer's disease patient having a cognitive impairment but exhibiting minimal or no apathy, comprising administering to the subject clomipramine or a pharmaceutically acceptable salt thereof.

In some embodiments, the present disclosure provides a method for treating a subject at a risk of developing AD, comprising administering to the subject clomipramine or a pharmaceutically acceptable salt thereof.

The administration of clomipramine or a pharmaceutically acceptable salt thereof to any of the subjects described herein reduces neurodegeneration, increases levels of TAp73, decreases levels of PCNA, and/or decreases levels of cleaved caspase-3 in neuronal cells of the subject. The fold change or the percent increase or decrease in the levels of TAp73, PCNA, and cleaved caspase-3 are described above.

In some embodiments, the administration of clomipramine or a pharmaceutically acceptable salt thereof improves the cognitive function, learning abilities, and/or memory in AD patients. In some embodiments, the administration of clomipramine or a pharmaceutically acceptable salt thereof improves a long-term and short-term memory.

The dosage regimen for clomipramine or a pharmaceutically acceptable salt thereof varies based on a variety of factors, such as, age, weight, sex and other medical conditions of the patient. In some embodiments, clomipramine or a pharmaceutically acceptable salt thereof is administered in an amount of about 1 mg to about 5 mg, including values and ranges thereof, per kilogram of body weight per day. In some embodiments, clomipramine or a pharmaceutically acceptable salt thereof is administered in an amount of about 1 mg to 4.5 mg, about 1 mg to about 4 mg, about 1 mg to about 3.5 mg, about 1 mg to about 3 mg, about 1 mg to about 2.5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, about 2 mg to about 5 mg, about 2 mg to about 4.5 mg, about 2 mg to about 4 mg, about 2 mg to about 3.5 mg, about 2 mg to about 3 mg, about 2.5 mg to about 5 mg, about 2.5 mg to about 4.5 mg, about 2.5 mg to about 4 mg, about 2.5 mg to about 3.5 mg, about 3 mg to about 5 mg, about 3 mg to about 4.5 mg, about 3 mg to about 4 mg, about 3.5 mg to about 5 mg, about 3.5 mg to about 4.5 mg, or about 4 mg to about 5 mg, including values and ranges thereof, per kilogram of body weight per day. In some embodiments, clomipramine or a pharmaceutically acceptable salt thereof is administered in an amount of about 1 mg to 3 mg per kg per day.

The total daily dose can be administered once or a plurality of times in a day. In some embodiments, clomipramine or a pharmaceutically acceptable salt thereof is administered orally.

For oral administration, clomipramine or a pharmaceutically acceptable salt thereof may be provided in the form of an oral dosage form containing 10 mg, 25 mg, 50 mg, or 75 mg of clomipramine or a pharmaceutically acceptable salt thereof. An oral dosage form containing clomipramine or a pharmaceutically acceptable salt thereof can be in the form of a tablet or a capsule.

In some embodiments, clomipramine is administered in the form of a coated tablet containing 10 mg or 25 mg of clomipramine hydrochloride. In some embodiments, the coated tablet of clomipramine hydrochloride comprises lactose monohydrate, Maize starch, Hypromellose (hydroxypropyl methylcellulose), Magnesium stearate, Silica colloidal anhydrous, Talc, Copovidone (vinylpyrrolidone/vinylacetate copolymer), Titanium dioxide (E171), Sucrose, Povidone (polyvinylpyrrolidone), Iron oxide, yellow (E172), macrogol 8000 (polyethylene glycol 8000), and Cellulose microcrystalline as excipients. In some embodiments, the coated tablet may also comprise stearic acid and glycerol (85%) as excipients.

In some embodiments, clomipramine is administered in the form of a sustained-release tablet (divisible and non-divisible) containing 75 mg clomipramine hydrochloride. In some embodiments, sustained-release, divisible tablets of clomipramine comprise calcium hydrogen phosphate dihydrate, Polyacrylate dispersion 30%, Calcium stearate, Silica colloidal anhydrous, Hypromellose (hydroxypropyl methylcellulose), Talc, Titanium dioxide, Macrogolglycerol hydroxystearate (polyoxyl 40 hydrogenated castor oil), and Iron oxide red as excipients.

In some embodiments, clomipramine is administered in the form of a capsule containing 10 mg, 25 mg or 50 mg clomipramine hydrochloride. In some embodiments, clomipramine hydrochloride capsules comprise lactose monohydrate, Maize starch, Talc, colloidal anhydrous Silica, and Magnesium stearate as excipients.

In some embodiments, the present disclosure provides use of clomipramine or a pharmaceutically acceptable salt thereof for treating AD. AD is a progressive disease and can be categorized into various stages based on the severity of symptoms as described herein. The present disclosure contemplates use of clomipramine or a pharmaceutically acceptable salt thereof for treating various stages of AD described herein. Dosage forms, dosages, and routes of administration of clomipramine or a pharmaceutically acceptable salt are discussed above.

In some embodiments, the present disclosure provides clomipramine or a pharmaceutically acceptable salt thereof or use as a medicament for treating various stages of AD. Dosage forms, dosages, and routes of administration that may be employed for the medicament are discussed above.

It is to be understood that the foregoing descriptive matter is illustrative of the disclosure and not a limitation. While considerable emphasis has been placed herein on the particular features of this disclosure, it will be appreciated that various modifications can be made, and that many changes can be made in the preferred embodiments without departing from the principles of the disclosure. Those skilled in the art will recognize that the embodiments herein can be practiced with modification within the spirit and scope of the embodiments as described herein. Similarly, additional embodiments and features of the present disclosure will be apparent to one of ordinary skill in art based upon description provided herein.

Descriptions of well-known/conventional methods/steps and techniques are omitted so as to not unnecessarily obscure the embodiments herein. Further, the disclosure herein provides for examples illustrating the above-described embodiments, and in order to illustrate the embodiments of the present disclosure certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Example 1: Clomipramine prevents TAp73 degradation and reverts CRNA

Figure 1B:
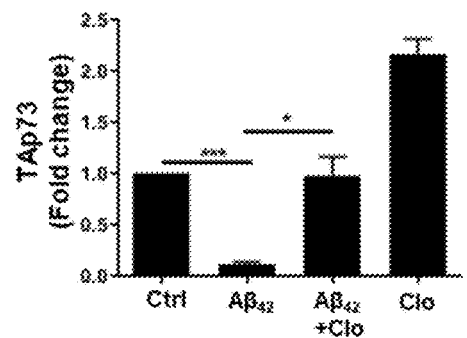
FIG. 1B shows the quantification of the levels of TAp73 from the Western blot of FIG. 1A (data represented as mean±SEM of three independent biological replicates).
Figure 1C:
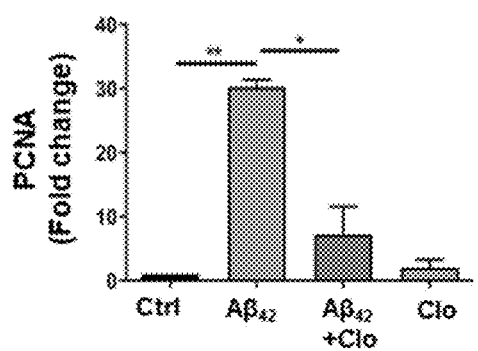
FIG. 1C the quantification of the levels of PCNA (proliferating cell nuclear antigen) from the Western blot of FIG. 1A (data represented as mean±SEM of three independent biological replicates).
Figure 1D:
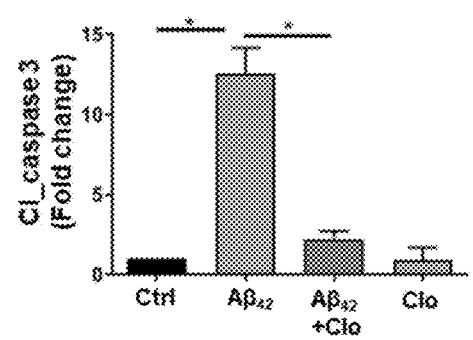
FIG. 1D shows the quantification of the levels of cleaved caspase-3 from the Western blot of FIG. 1A (data represented as mean±SEM of three independent biological replicates).

The effect of clomipramine on cell cycle related neuronal apoptosis (CRNA) was investigated in Aβ42-treated cortical neurons (Aβ42 peptide induces neurodegeneration in AD patients). The TAp73 levels were restored upon clomipramine treatment (FIG. 1A). Clomipramine caused a significant decrease in PCNA and cleaved caspase 3 which suggested a reversal of cell cycle re-entry and apoptosis respectively (FIG. 1A). FIGS. 1B, 1C, and 1D show the quantification of TAp73, PCNA, and cleaved caspase-3 levels of the Western blot of FIG. 1A.

Figure 2A:
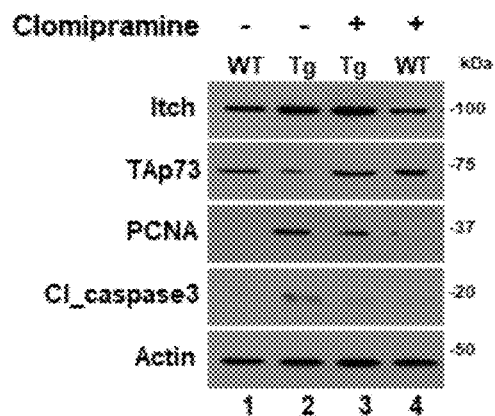
FIG. 2A shows a Western blot of mouse cortical neurons lysate from WT or AD transgenic mouse model (Tg) treated with clomipramine.
Figure 2B:
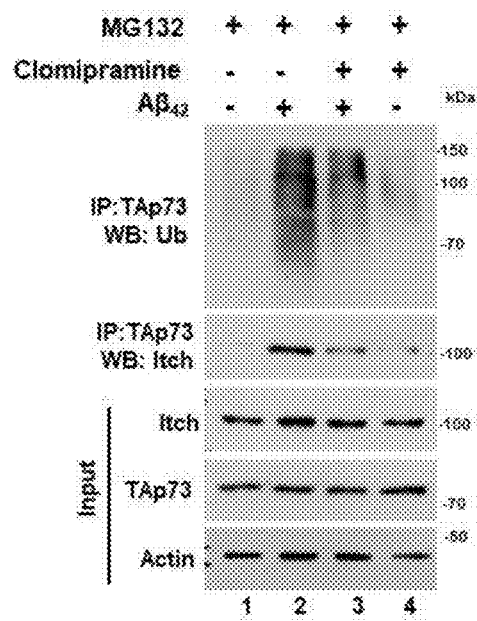
FIG. 2B shows a Western blot of immunoprecipitated TAp73 for ubiquitination in rat cortical neurons treated with Aβ-42 peptide followed by clomipramine in presence of MG132, proteasome inhibitor.

The effect of clomipramine on cell cycle related neuronal apoptosis (CRNA) was also explored in AD transgenic mouse model (Tg) cortical neurons (in this mouse model, there is an increased production of Aβ42 which induces neurodegeneration similar to AD patients). The TAp73 levels were restored upon clomipramine treatment (FIG. 2A) in these Tg neurons lysate which resulted in a significant decrease in PCNA and cleaved caspase 3 suggesting a reversal of cell cycle re-entry and apoptosis respectively (FIG. 2A). In addition, when TAp73 was immunoprecipitated in presence of proteasomal inhibitor, MG132; the treatment of clomipramine showed less ubiquitination of TAp73 (FIG. 2B).

Figure 3A:
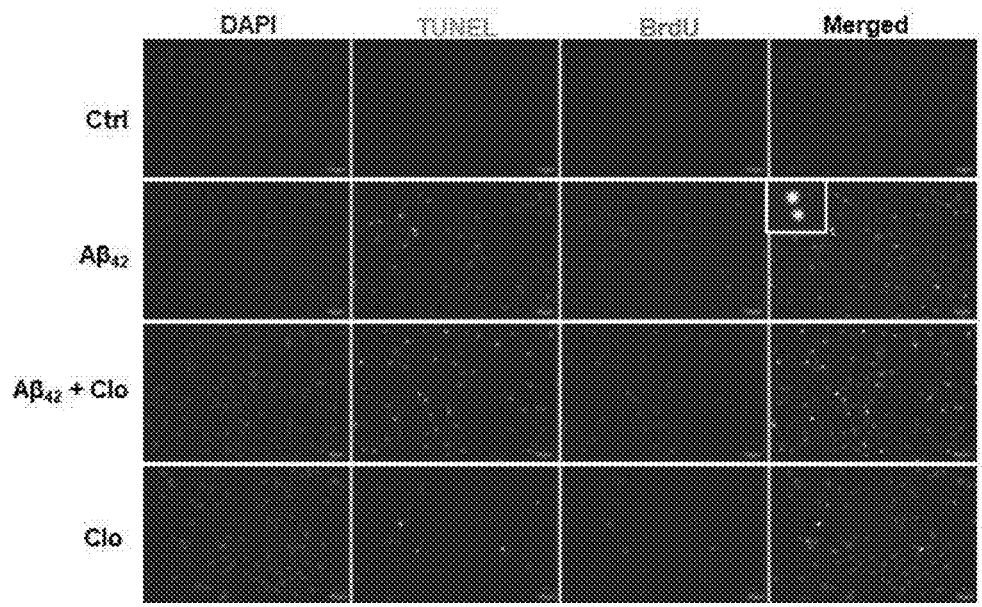
FIG. 3A shows fluorescence microscope images of the BrdU/Tunnel assay on cortical neurons treated with Aβ-42 peptide and clomipramine.
Figure 3B:
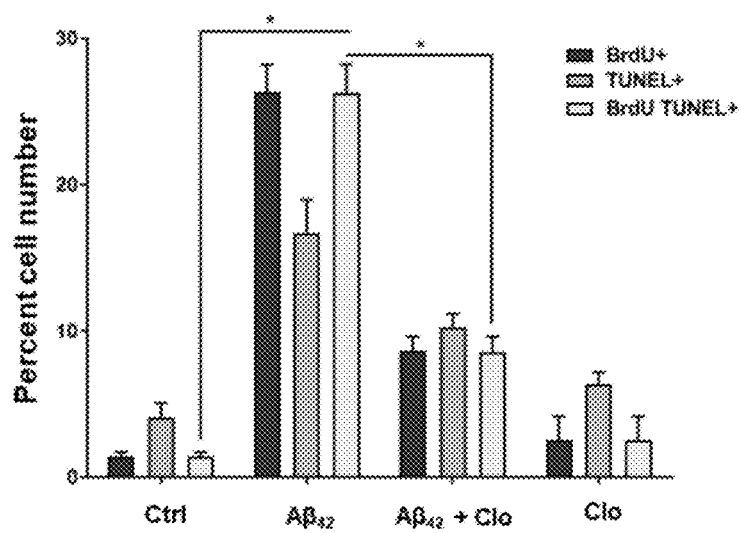
FIG. 3B shows the quantification of the percent cell number for the BrdU/Tunnel assay in FIG. 3A (data represented as mean±SEM of three independent biological replicates).

Subsequently, BrdU incorporation and TUNEL labelling was performed to detect DNA replication and apoptosis, respectively. A significant reduction in BrdU+/TUNEL+ cells upon clomipramine treatment of Aβ42 treated cortical neurons was observed which confirmed the reversal of CRNA (FIGS. 3A and 3B). These findings indicate that clomipramine inhibits CRNA in AD neurons by preventing TAp73 degradation.

Figure 3C:
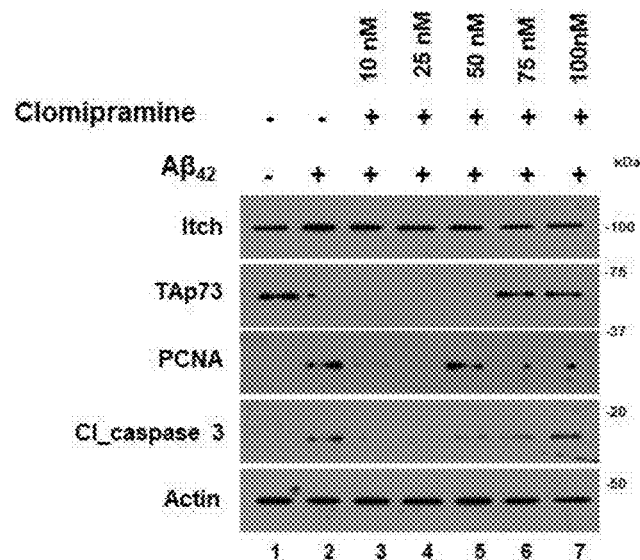
FIG. 3C shows a Western blot of lysates obtained from rat cortical neurons treated with Aβ-42 peptide followed by varying concentration of clomipramine.

To determine an effective concentration of clomipramine, Aβ42 treated rat cortical neurons were subjected to different concentrations (10 nM to 100 nM) of clomipramine for 48 h. Lysates were prepared and immunoblotting was performed. The restoration in TAp73 levels was observed in 75 and 100 nM concentrations of clomipramine treatment (FIG. 3C).

Figure 3D:
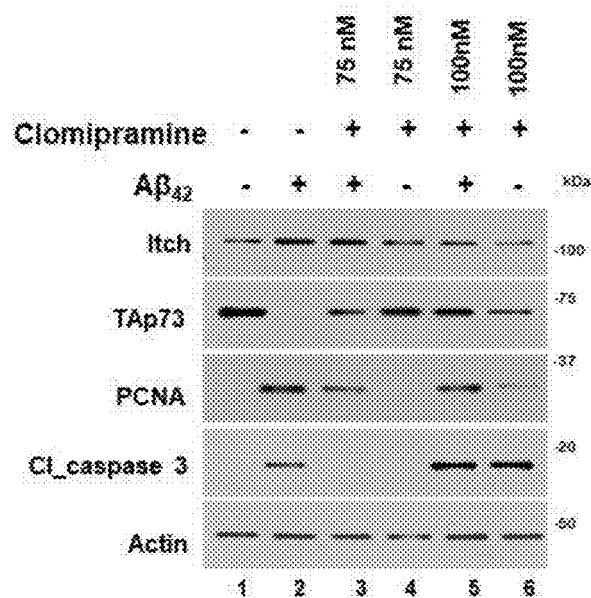
FIG. 3D shows a Western blot of lysates obtained from rat cortical neurons treated with Aβ-42 peptide and 75 nM or 100 nM clomipramine.
Figure 3E:
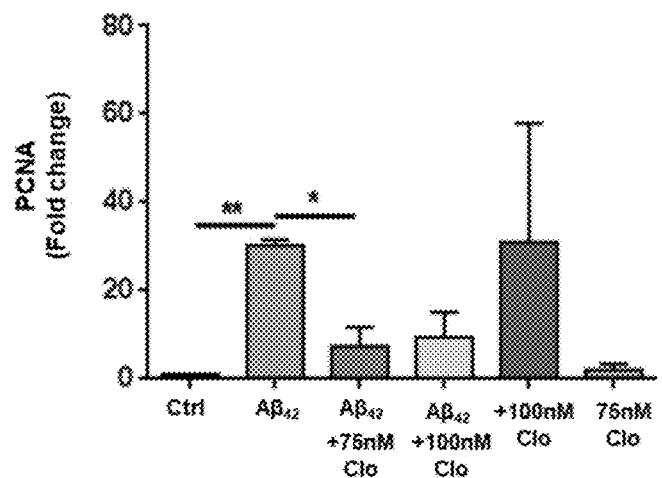
FIG. 3E shows the quantification of the levels of PCNA from the Western blot of FIG. 3D (data represented as mean±SEM of three independent biological replicates).
Figure 3F:
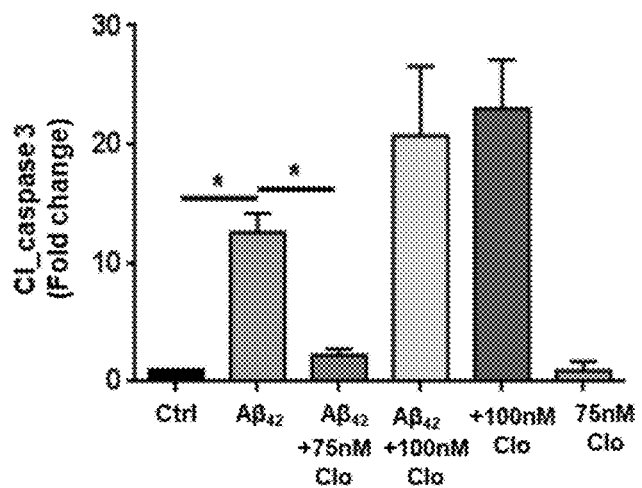
FIG. 3F shows the quantification of the levels of cleaved caspase-3 from the Western blot of FIG. 3D (data represented as mean±SEM of three independent biological replicates).

Next, two sets of Aβ42 treated rat cortical neurons were subjected to two different concentrations of clomipramine— 75 nM to 100 nM (at which maximum TAp73 restoration was observed in the previous experiment). After 48 h, one set of cells were lysed, lysates were prepared and the lysates were subjected to immunoblotting. The treatment with 75 nM clomipramine was found to be effective in reducing cell cycle related neuronalapoptosis while with 100 nM concentration of clomipramine, more apoptosis was observed (FIG. 3D, FIGS. 3E and 3F show the quantification of the data in FIG. 3D).

Figure 3G:
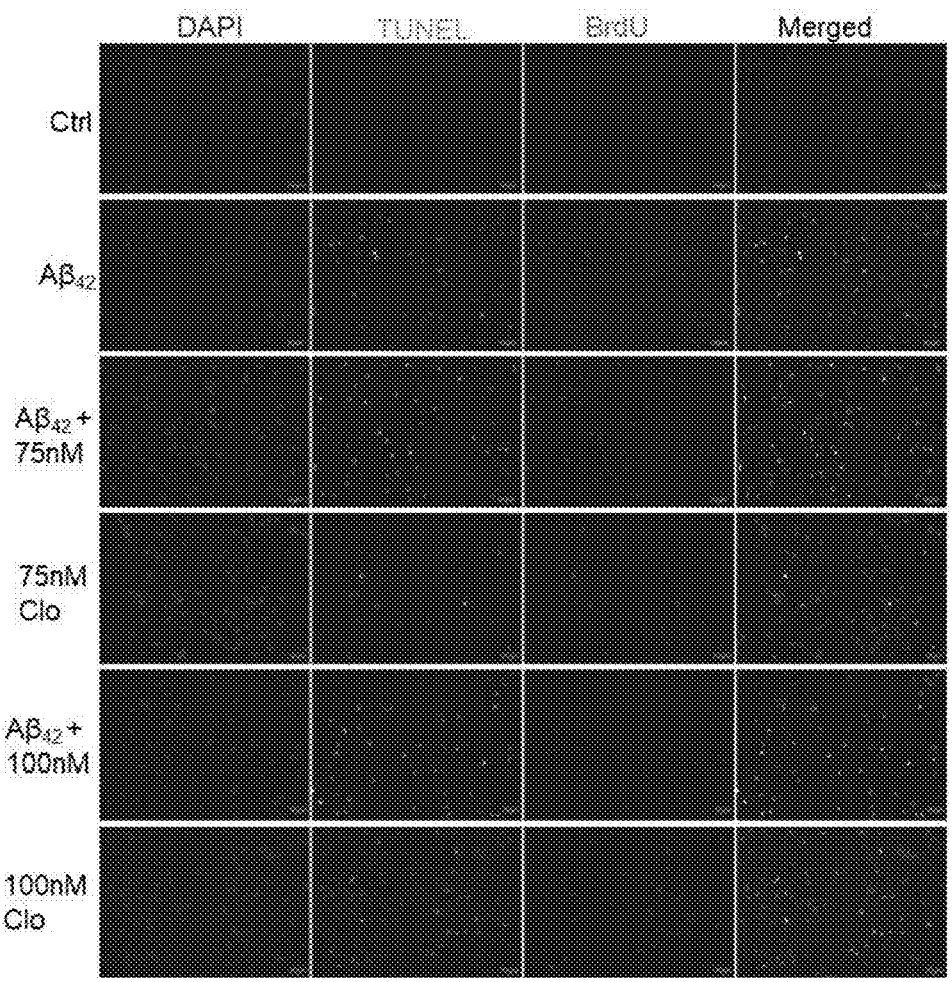
FIG. 3G shows fluorescence microscope images of the BrdU/Tunnel assay on cortical neurons treated with Aβ-42 peptide and 75 nM or 100 nM clomipramine.
Figure 3H:
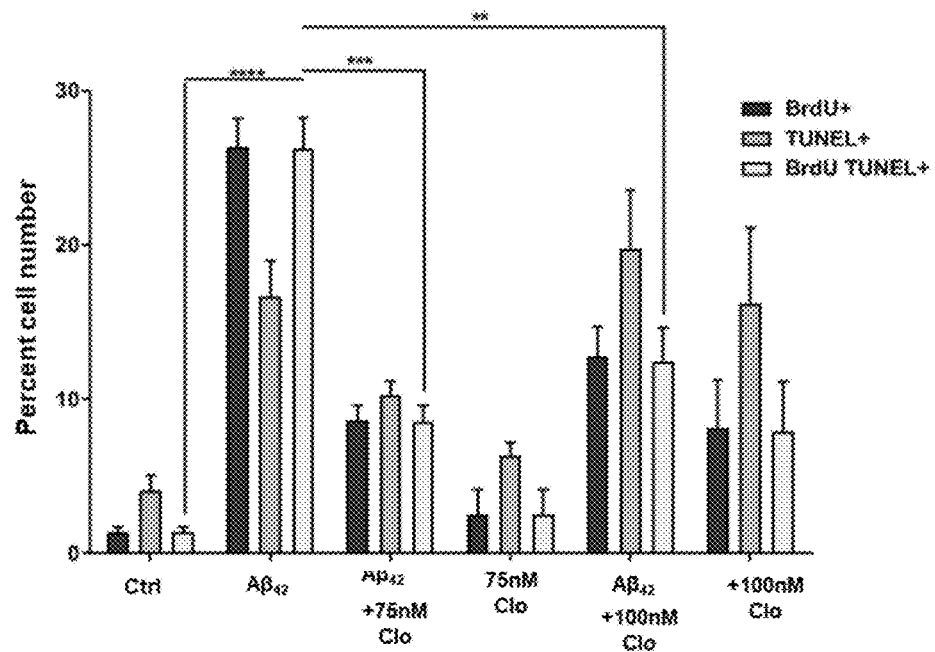
FIG. 3H shows the quantification of the cell number for the BrdU/Tunnel assay from FIG. 3G (data represented as mean±SEM of three independent biological replicates).

To another set of cells, BrdU was added after 48 h to label the neurons undergoing the replication (cell cycle re-entry). After that TUNEL assay was performed to label the cells undergoing apoptosis (FIG. 3G). The number of double positive cells were scored and plotted in the graph (FIG. 3H). Similar to the western blotting, 75 nM concentration of clomipramine was found to more potent in preventing CRNA.

Example 2: Clomipramine Improves Cognition Defects in TgAD Mice (Mouse Model of AD)

Next, the effect of clomipramine was tested in an in vivo mouse model of AD. For this, Amyloid Precursor Protein (APP)/Presenillin 1 (PS1) transgenic (TgAD) mouse model for AD (strain name B6C3-Tg APPswe, PSEN1dE9 85Dboa; stock number 004462) was used. Wild type and transgenic (TgAD) mice were genotyped using genomic DNA isolated from mouse tail and PCR primers according to the Jackson laboratory protocol. Clomipramine hydrochloride, obtained from Sigma (C-7291), was dissolved in ultrapure MQ just before the injection and 100 μl of this solution was injected intraperitonially (I.P.injections) to each mouse of 23-25 g in weight (25 mg/kg body weight) for 45 days. Various behaviour tests (Morris water maze, Y-maze and Radial arm maze) were performed on clomipramine/saline injected mice.

Behavioural Tests:

For Morris water maze test, animals were subjected to three trials per session and one session a day, for five days. Each trial was for 60 s in which mice had to reach the hidden platform in the water, and the average time per session was recorded as escape latency. After the escape training, the platform was removed for the probe trial test. It tested the retention of spatial memory at 24 h after training (Vorhees and Williams 2006, Nunez 2008). The number of times a mouse crossed the probe, the time spent in the target quadrant, and swim speed were recorded using ANY-maze software (Stoelting Co., USA).

For Y-Maze test, animals were habituated in the Y-shaped maze for 3 min with one of the arms blocked then their spontaneous alternations were recorded with all arms open for 5 min (Miedel, Patton et al. 2017). The number of alternations was recorded manually and percent spontaneous alternations were calculated as mentioned below:

Percentage spontaneous alternation (SA)=(No. of alternations/(No. of arm entries−2)*100

For radial arm (8-arm) maze test, mice were given restricted amount of food until their bodyweight reduced to 85% of the initial weight for two days prior to habituation in the maze. In habituation phase, each mouse was allowed to explore and consume food pellets scattered on the whole maze for a 10 min period (one session per mouse). In the training phase, three arms were blocked and the remaining five alternate arms were baited. On the test day, all arms were opened and same five arms were baited as in trial sessions and their series of entries were recorded manually (Miyakawa, Yamada et al. 2001), from which the percentage of working and reference memory errors were calculated.

The mouse entering an arm containing food where it had previously entered, was counted as working memory error (short term memory) and if the mouse entered in an arm without bait, was counted as reference memory error (long term memory for position of the baited arms).

Figure 4A:
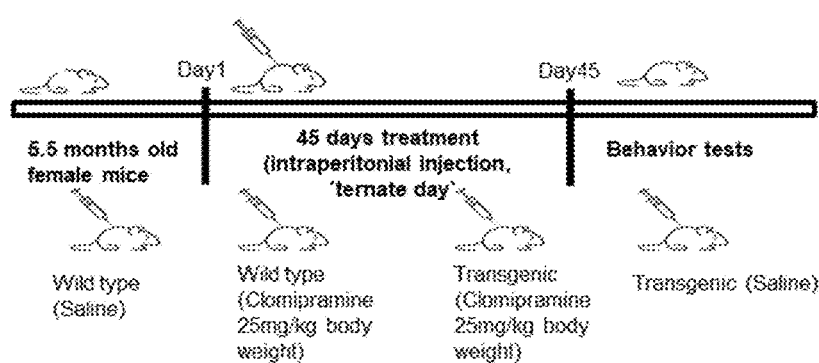
FIG. 4A shows a schematic of the treatment regimen of WT and TgAD mice with clomipramine.
Figure 4B:
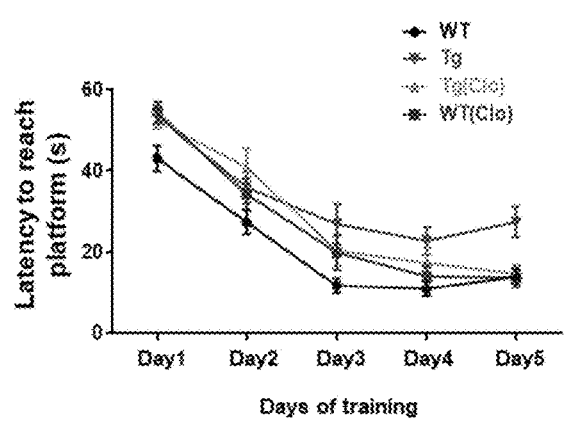
FIG. 4B shows the compiled results of the Morris water maze test of WT and TgAD mice treated with clomipramine for five days
Figure 4C:
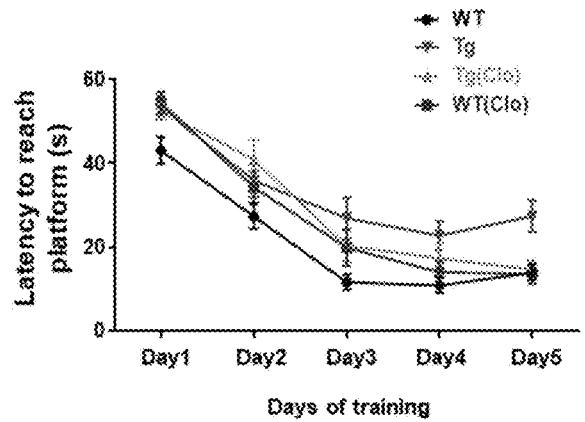
FIG. 4C shows the results of the Morris water maze test of WT and TgAD mice treated with clomipramine on final day.
Figure 5A:
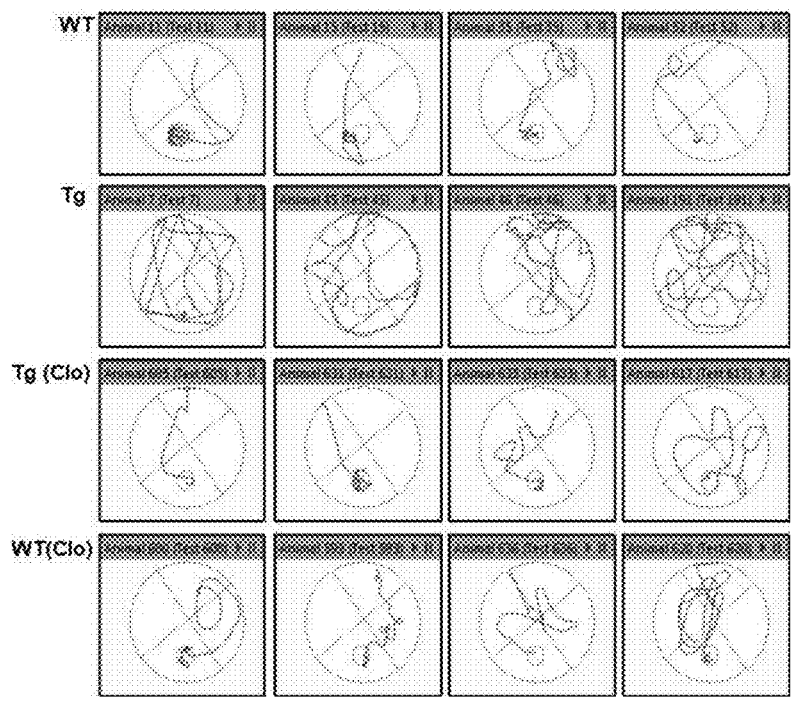
FIG. 5A shows representative track plots of WT and TgAD mice treated with clomipramine from the Morris water maze test.

For in vivo studies, ~6 months old WT/TgAD mice were intraperitonially injected with 25 mg/kg body weight of clomipramine for 45 days (FIG. 4A) and subjected to various behavior tests. In Morris water maze test, vehicle/saline treated TgAD mice took significantly more time than the WT animals to reach the platform as referred previously (Nunez 2008). Upon administration of clomipramine, TgAD mice showed marked improvement (FIG. 4B) and were almost similar to the WT mice on the last day of training (FIGS. 4B, 4C and 5A). After five days of training, probe trial was performed and observed that WT mice spent lesser time searching for the platform in the area of previous location (target quadrant) than the TgAD reflected by FIG. 5B. In contrast, clomipramine treated TgAD mice crossed the target quadrant area more frequently, almost similar to WT mice. These observations indicate improved spatial learning in TgAD mice upon clomipramine treatment.

Figure 7A:
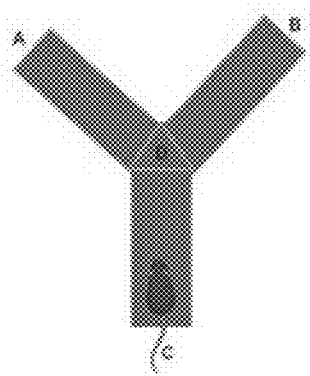
FIG. 7A shows a schematic of the Y-maze for the Y-maze test.
Figure 7B:
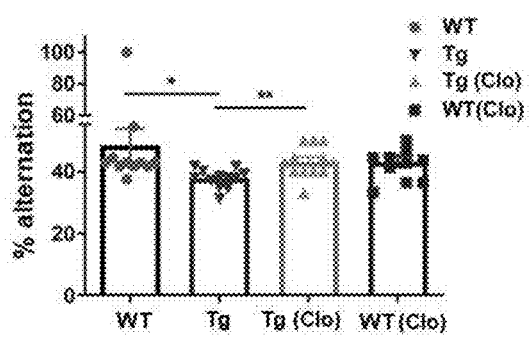
FIG. 7B shows the results of the Y-maze test of WT and TgAD mice treated with clomipramine.
Figure 7C:
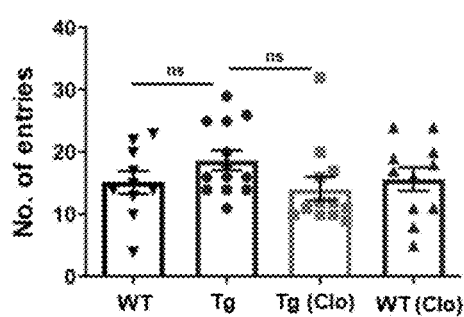
FIG. 7C shows the total number of arm entries in the Y-maze test of WT and TgAD mice treated with clomipramine.

Y-maze test is an initial test of memory function. It is generally used to determine whether animal prefers to spend time in a novel or familiar area (Momeni, Segerstrom et al. 2015, Yan, He et al. 2017). To test this, one arm of the Y-Maze was blocked and the mouse was allowed to explore the other two arms. The memory function was tested when the animal was returned to the maze with all arms open and the tendency to spend time in the new or familiar arms was monitored. TgAD mice exhibited reduced alternation in comparison to the WT counterparts and an improvement of spontaneous alternation in clomipramine treated TgAD mice group was observed as compared to the TgAD (FIG. 7A). However, no significant changes were observed in the total number of arm entries made by each group (FIG. 7C).

Figure 8A:
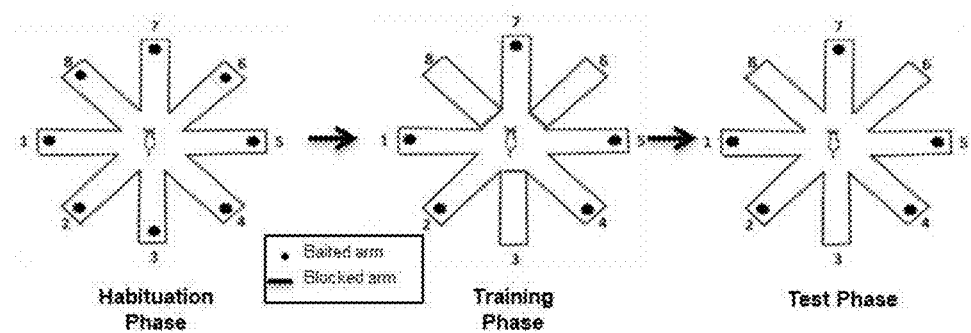
FIG. 8A shows a schematic of the radial arm maze test.
Figure 8B:
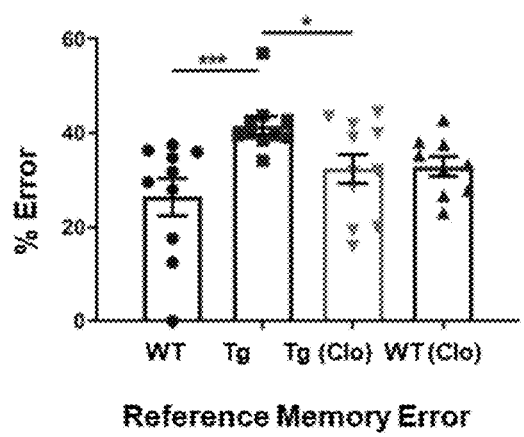
FIG. 8B shows the reference memory error results of the radial arm maze test WT and TgAD mice treated with clomipramine.
Figure 8C:
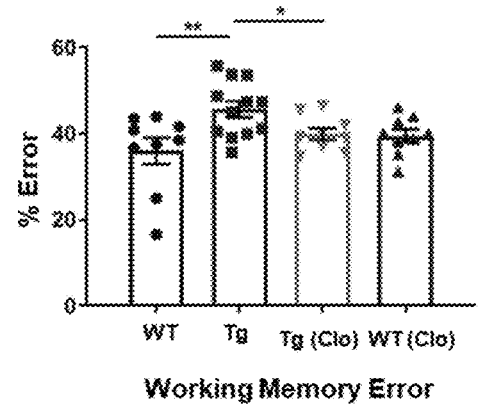
FIG. 8C shows the working memory error results of the radial arm maze test WT and TgAD mice treated with clomipramine.

Radial arm maze test was also performed to assess the long term as well as short term memory of mice (Penley, Gaudet et al. 2013, Fredriksson, Sreedharan et al. 2019). For this purpose, the 24 h food deprived mice were placed on the central platform of 8-arm maze and allowed to explore the maze for food (bait) placed at the end of each arm as depicted in FIG. 8A. Each training/testing session was 10 min long. The number of times a mouse entering a baited arm that has been previously visited were recorded and scored as working memory error while the entry into the previously blocked arms was regarded as a reference memory error. TgAD mice group committed more reference and working memory errors than WT. Strikingly, there was a significant improvement in the clomipramine treated TgAD mice (FIGS. 8B and 8C). No significant differences in the food intake, water intake, were observed among the 4 groups of mice treated with clomipramine and saline. The body weight (FIG. 6B), swimming speed (FIG. 6A) as well as learning and memory abilities between the 2 groups of wild-type mice treated with clomipramine and saline was almost unchanged (FIGS. 4B, 4C, 5B, 7B, 8B, and 8C; $p>0.05$, respectively). Based on these observations, it appears that chronic treatment with clomipramine had no major side effects in mice.

Collectively, these data indicated that clomipramine treatment ameliorated cognitive deficits like spatial learning and memory in TgAD mice following six weeks of treatment with clomipramine.

Example 3: Clomipramine-Treated Mice Exhibit Reduced CRNA

The animals used in the above-mentioned behavioral tests were euthanized and cortex region of brain was dissected out for biochemical analysis. The levels of Itch, TAp73, PCNA and cleaved caspase-3 were determined with Western blotting (FIG. 9A). FIGS. 9B-9F show the quantification of the levels of Itch, TAp73, PCNA and cleaved caspase-3 of the Western blot of FIG. 9A. After analysis of six animals from each group, it was observed that TAp73 protein levels, which were reduced in TgAD cortex, were much higher in clomipramine treated TgAD brains. These data suggested that this inhibitor does prevent TAp73 degradation in vivo. Importantly, CRNA which is exacerbated in TgAD cortex was reversed in clomipramine-treated mice as indicated by decrease in PCNA and cleaved caspase 3 (FIG. 9A). These results suggested that clomipramine rescued TAp73 from Itch mediated degradation thereby inhibiting CRNA and leading to improvements in cognition in TgAD mice.

Numbered Embodiments of the Disclosure

1. A method for treating Alzheimer's disease in a patient in need thereof, comprising administering to the patient clomipramine or a pharmaceutically acceptable salt thereof
2. The method of Embodiment 1, wherein administration of clomipramine to the patient inhibits degradation of TAp73 in neuronal cells of the patient by about 0.5 to about 2-fold compared to levels of TAp73 prior to administration of clomipramine.
3. The method of Embodiment 1, wherein administration of clomipramine to the patient inhibits degradation of TAp73 in neuronal cells of the patient by about 20-70% compared to levels of TAp73 prior to administration of clomipramine.
4. The method of any one of Embodiments 1-3, wherein administration of clomipramine to the patient inhibits cell cycle related neuronal apoptosis (CRNA) in the patient by about 0.5 to 5-fold as measured by a decrease in levels of proliferating cell nuclear antigen (PCNA) when compared to levels of PCNA prior to administration of clomipramine.
5. The method of any one of Embodiments 1-3, wherein administration of clomipramine to the patient inhibits cell cycle related neuronal apoptosis (CRNA) in the patient by about 20-90% as measured by a decrease in levels of proliferating cell nuclear antigen (PCNA) when compared to levels of PCNA prior to administration of clomipramine.
6. The method of any one of Embodiments 1-5, wherein administration of clomipramine to the patient improves short-term and long-term memory in the patient.
7. The method of any one of Embodiments 1-6, wherein clomipramine is administered to the patient in an amount of about 1 to 5 mg/kg/day.
8. A method of reducing neurodegeneration in a patient suffering from Alzheimer's disease or at a risk of developing Alzheimer's disease, comprising administering to the patient clomipramine or a pharmaceutically acceptable salt thereof
9. The method of Embodiment 8, wherein administration of clomipramine to the patient reduces neurodegeneration in the patient by inhibiting degradation of TAp73 in neuronal cells of the patient by about 0.5 to about 2-fold compared to levels of TAp73 prior to administration of clomipramine.
10. The method of Embodiment 8, wherein administration of clomipramine to the patient reduces neurodegeneration in the patient by inhibiting degradation of TAp73 in neuronal cells of the patient by about 20-90% compared to levels of TAp73 prior to administration of clomipramine.

11. The method of any one of Embodiments 8-10, wherein administration of clomipramine to the patient reduces neurodegeneration in the patient by inhibiting cell cycle related neuronal apoptosis (CRNA) in the patient by about 0.5 to 5-fold as measured by a decrease in levels of proliferating cell nuclear antigen (PCNA) when compared to levels of PCNA prior to administration of clomipramine.

12. The method of any one of Embodiments 8-10, wherein administration of clomipramine to the patient reduces neurodegeneration in the patient by inhibiting cell cycle related neuronal apoptosis (CRNA) in the patient by about 20-90% as measured by a decrease in levels of proliferating cell nuclear antigen (PCNA) when compared to levels of PCNA prior to administration of clomipramine.

13. A method for treating an Alzheimer's disease patient having a cognitive impairment but minimal or no anxiety, comprising administering to the patient clomipramine or a pharmaceutically acceptable salt thereof 14. A method for treating a mild cognitive impairment (MCI) in a patient, comprising administering to the patient clomipramine or a pharmaceutically acceptable salt thereof 15. A method of treating an Alzheimer's Disease (AD) patient having a Clinical Dementia Rating Scale Sum of Boxes (CDR-SOB) score from 4.5 to 9.0, comprising administering to the patient clomipramine or a pharmaceutically acceptable salt thereof 16. A method of treating an Alzheimer's Disease (AD) patient having a Clinical Dementia Rating Scale Sum of Boxes (CDR-SOB) score from 9.5 to 15.5, comprising administering to the patient clomipramine or a pharmaceutically acceptable salt thereof 17. A method of treating an Alzheimer's Disease (AD) patient having a Clinical Dementia Rating Scale Sum of Boxes (CDR-SOB) score from 16 to 18, comprising administering to the patient clomipramine or a pharmaceutically acceptable salt thereof 18. A method for treating a pre-clinical stage Alzheimer's Disease (AD) in a patient, comprising administering to the patient clomipramine or a pharmaceutically acceptable salt thereof 19. The method of any one of Embodiments 13-18, wherein administration of clomipramine to the patient inhibits degradation of TAp73 in neuronal cells of the patient by about 0.5 to about 2-fold compared to levels of TAp73 prior to administration of clomipramine.

20. The method of any one of Embodiments 13-18, wherein administration of clomipramine to the patient inhibits degradation of TAp73 in neuronal cells of the patient by about 20-70% compared to levels of TAp73 prior to administration of clomipramine.

21. The method of any one of Embodiments 13-18, wherein administration of clomipramine to the patient inhibits cell cycle related neuronal apoptosis (CRNA) in the patient by about 0.5 to 5-fold as measured by a decrease in levels of proliferating cell nuclear antigen (PCNA) when compared to levels of PCNA prior to administration of clomipramine.

22. The method of any one of Embodiments 13-18, wherein administration of clomipramine to the patient inhibits cell cycle related neuronal apoptosis (CRNA) in the patient by about 20-90% as measured by a decrease in levels of proliferating cell nuclear antigen (PCNA) when compared to levels of PCNA prior to administration of clomipramine.

23. The method of any one of Embodiments 13-18, wherein clomipramine is administered to the patient in an amount of about 1 to 5 mg/kg/day.

24. A composition comprising clomipramine or a pharmaceutically acceptable salt thereof for use as a medicament for treating Alzheimer's disease in a patient in need thereof 25. A composition comprising clomipramine or a pharmaceutically acceptable salt thereof for use as a medicament for treating an Alzheimer's disease patient having a cognitive impairment but minimal or no anxiety.

26. A composition comprising clomipramine or a pharmaceutically acceptable salt thereof for use as a medicament for treating a mild cognitive impairment (MCI) in a patient.

27. A composition comprising clomipramine or a pharmaceutically acceptable salt thereof for use as a medicament for treating an Alzheimer's Disease (AD) patient having a Clinical Dementia Rating Scale Sum of Boxes (CDR-SOB) score from 4.5 to 9.0.

28. A composition comprising clomipramine or a pharmaceutically acceptable salt thereof for use as a medicament for treating an Alzheimer's Disease (AD) patient having a Clinical Dementia Rating Scale Sum of Boxes (CDR-SOB) score from 9.5 to 15.5.

29. A composition comprising clomipramine or a pharmaceutically acceptable salt thereof for use as a medicament for treating an Alzheimer's Disease (AD) patient having a Clinical Dementia Rating Scale Sum of Boxes (CDR-SOB) score from 16 to 18.

30. A composition comprising clomipramine or a pharmaceutically acceptable salt thereof for use as a medicament for treating a pre-clinical stage of Alzheimer's Disease (AD).

31. The composition for use as recited in any one of Embodiments 24-30, wherein administration of clomipramine to the patient inhibits degradation of TAp73 in neuronal cells of the patient by about 0.5 to about 2-fold compared to levels of TAp73 prior to administration of clomipramine.

32. The composition for use as recited in any one of Embodiments 24-30, wherein administration of clomipramine to the patient inhibits degradation of TAp73 in neuronal cells of the patient by about 20-70% compared to levels of TAp73 prior to administration of clomipramine.

33. The composition for use as recited in any one of Embodiments 24-32, wherein administration of clomipramine to the patient inhibits cell cycle related neuronal apoptosis (CRNA) in the patient by about 0.5 to 5-fold as measured by a decrease in levels of proliferating cell nuclear antigen (PCNA) when compared to levels of PCNA prior to administration of clomipramine.

34. The composition for use as recited in any one of Embodiments 24-32, wherein administration of clomipramine to the patient inhibits cell cycle related neuronal apoptosis (CRNA) in the patient by about 20-90% as measured by a decrease in levels of proliferating cell nuclear antigen (PCNA) when compared to levels of PCNA prior to administration of clomipramine.

35. The composition for use as recited in any one of Embodiments 24-34, wherein administration of clomipramine to the patient improves short-term and long-term memory in the patient.

36. The composition for use as recited in any one of Embodiments 24-35, wherein the composition comprises about 10 mg, 25 mg, 50 mg, or 75 mg of clomipramine or a pharmaceutically acceptable salt thereof 37. Use of clomipramine or a pharmaceutically acceptable salt thereof for treating Alzheimer's disease in a patient in need thereof 38. Use of clomipramine or a pharmaceutically acceptable salt thereof for treating an Alzheimer's disease patient having a cognitive impairment but minimal or no anxiety.

39. Use of clomipramine or a pharmaceutically acceptable salt thereof for treating a mild cognitive impairment (MCI) in a patient.

40. Use of clomipramine or a pharmaceutically acceptable salt thereof for treating an Alzheimer's Disease (AD) patient having a Clinical Dementia Rating Scale Sum of Boxes (CDR-SOB) score from 4.5 to 9.0.

41. Use of clomipramine or a pharmaceutically acceptable salt thereof for treating an Alzheimer's Disease (AD) patient having a Clinical Dementia Rating Scale Sum of Boxes (CDR-SOB) score from 9.5 to 15.5.

42. Use of clomipramine or a pharmaceutically acceptable salt thereof for treating an Alzheimer's Disease (AD) patient having a Clinical Dementia Rating Scale Sum of Boxes (CDR-SOB) score from 16 to 18.

43. Use of clomipramine or a pharmaceutically acceptable salt thereof for treating a pre-clinical stage of Alzheimer's Disease (AD).

The invention claimed is:

1. A method for treating Alzheimer's disease in a patient in need thereof, comprising administering to the patient clomipramine or a pharmaceutically acceptable salt thereof, wherein administration of clomipramine to the patient inhibits cell cycle related neuronal apoptosis (CRNA) in the patient by about 20-90% as measured by a decrease in levels of proliferating cell nuclear antigen (PCNA) when compared to levels of PCNA prior to administration of clomipramine.

2. The method of claim 1, wherein administration of clomipramine to the patient inhibits degradation of TAp73 in neuronal cells of the patient by about 0.5 to about 2-fold compared to levels of TAp73 prior to administration of clomipramine.

3. The method of claim 1, wherein administration of clomipramine to the patient inhibits degradation of TAp73 in neuronal cells of the patient by about 20-70% compared to levels of TAp73 prior to administration of clomipramine.

4. The method of claim 1, wherein administration of clomipramine to the patient inhibits cell cycle related neuronal apoptosis (CRNA) in the patient by about 0.5 to 5-fold as measured by a decrease in levels of proliferating cell nuclear antigen (PCNA) when compared to levels of PCNA prior to administration of clomipramine.

5. The method of claim 1, wherein administration of clomipramine to the patient improves short-term and long-term memory in the patient.

6. The method of claim 1, wherein clomipramine is administered to the patient in an amount of about 1 to 5 mg/kg/day.

7. The method of claim 1, wherein clomipramine is administered to the patient in the form of clomipramine hydrochloride.

8. A method of reducing neurodegeneration in a patient suffering from Alzheimer's disease or at a risk of developing Alzheimer's disease, comprising administering to the patient clomipramine or a pharmaceutically acceptable salt thereof, wherein administration of clomipramine to the patient inhibits cell cycle related neuronal apoptosis (CRNA) in the patient by about 20-90% as measured by a decrease in levels of proliferating cell nuclear antigen (PCNA) when compared to levels of PCNA prior to administration of clomipramine.

9. The method of claim 8, wherein administration of clomipramine to the patient reduces neurodegeneration in the patient by inhibiting degradation of TAp73 in neuronal cells of the patient by about 0.5 to about 2-fold compared to levels of TAp73 prior to administration of clomipramine.

10. The method of claim 8, wherein administration of clomipramine to the patient reduces neurodegeneration in the patient by inhibiting degradation of TAp73 in neuronal cells of the patient by about 20-90% compared to levels of TAp73 prior to administration of clomipramine.

11. The method of claim 8, wherein administration of clomipramine to the patient reduces neurodegeneration in the patient by inhibiting cell cycle related neuronal apoptosis (CRNA) in the patient by about 0.5 to 5-fold as measured by a decrease in levels of proliferating cell nuclear antigen (PCNA) when compared to levels of PCNA prior to administration of clomipramine.

12. The method of claim 8, wherein clomipramine is administered to the patient in the form of clomipramine hydrochloride.

13. A method for treating a mild cognitive impairment (MCI) in a patient, comprising administering to the patient clomipramine or a pharmaceutically acceptable salt thereof, wherein administration of clomipramine to the patient inhibits cell cycle related neuronal apoptosis (CRNA) in the patient by about 20-90% as measured by a decrease in levels of proliferating cell nuclear antigen (PCNA) when compared to levels of PCNA prior to administration of clomipramine.

14. The method of claim 13, wherein administration of clomipramine to the patient inhibits degradation of TAp73 in neuronal cells of the patient by about 0.5 to about 2-fold compared to levels of TAp73 prior to administration of clomipramine.

15. The method of claim 13, wherein administration of clomipramine to the patient inhibits degradation of TAp73 in neuronal cells of the patient by about 20-70% compared to levels of TAp73 prior to administration of clomipramine.

16. The method of claim 13, wherein administration of clomipramine to the patient inhibits cell cycle related neuronal apoptosis (CRNA) in the patient by about 0.5 to 5-fold as measured by a decrease in levels of proliferating cell nuclear antigen (PCNA) when compared to levels of PCNA prior to administration of clomipramine.

17. The method of claim 13, wherein clomipramine is administered to the patient in an amount of about 1 to 5 mg/kg/day.

* * * * *